United States Patent [19]
Junge et al.

[11] 3,931,300
[45] Jan. 6, 1976

[54] PROCESS FOR THE PRODUCTION OF DICHLOROBENZOIC ACIDS

[75] Inventors: Helmut Junge, Wachenheim; Hans-Juergen Quadbeck-Seeger, Ludwigshafen, both of Germany

[73] Assignee: BASF Aktiengesellschaft, Ludwigshafen (Rhine), Germany

[22] Filed: Apr. 8, 1974

[21] Appl. No.: 458,766

[30] Foreign Application Priority Data
Apr. 11, 1973  Germany............................. 2318106

[52] U.S. Cl............................ 260/515 A; 260/141
[51] Int. Cl.$^2$......................................... C07C 63/12
[58] Field of Search............................... 260/515 A

[56] References Cited
OTHER PUBLICATIONS
Muller et al., Berichte, Vol. 74 (1941), p. 823.

Kornblum, Org. Reactions, Vol. 2 (1944), pp. 267, 274.

Primary Examiner—James A. Patten
Attorney, Agent, or Firm—Johnston, Keil, Thompson & Shurtleff

[57] ABSTRACT

The production of dichlorobenzoic acids by reaction of the diazonium compound of a dichloroaminobenzoic acid with an aqueous alcohol solution of specific concentration. The compounds which can be prepared according to the process of the invention are valuable starting materials for the production of pharmaceutical substances, dyes and pesticides.

11 Claims, No Drawings

PROCESS FOR THE PRODUCTION OF DICHLOROBENZOIC ACIDS

The invention relates to a process for the production of dichlorobenzoic acids by reaction of the diazonium compound of a dichloroaminobenzoic acid with an aqueous alcohol solution of a specified concentration.

It is known from Houben-Weyl, "Methoden der organischen Chemie", volume 10/3, pages 116 et seq., that aromatic diazonium salts can be converted by heating in alcohols into the corresponding aromatic hydrocarbons; it is recommended that the diazonium salt solutions used should be as concentrated as possible and that the amount of alcohol should be from five to ten times the volume thereof. The alcohol is thus converted into the corresponding aldehyde and the content of aldehyde thus increased prevents reuse of the unreacted portion of the alcohol. Depending on the constitution of the diazonium salt it is necessary to use anhydrous alcohol or an 80% by weight aqueous ethanol solution may be used. Organic Reactions, volume II, page 274 (Wiley, N.Y.) similarly teaches that although it is not essential for the reaction to be carried out in the absence of water the amount of water should not be more than about 5 to 10%.

In addition to the hydrocarbons there are also formed as byproducts the phenol ethers coresponding to the alcohol used (Houben-Weyl, loc.cit., page 124), particularly in alcohol diluted with water. The yield and purity of the end products are usually unsatisfactory, especially when the process is carried out on an industrial scale. Thus for example a yield of 46% of end product is given for 2,4-dichloroaniline as the starting amine and of 53% for anthranilic acid (Houben-Weyl, loc.cit., page 125). An article in Angewandte Chemie, volume 70 (1958), page 211, discloses that ethers such as dioxane have to be used instead of alcohols to avoid the formation of byproducts and the improve the yield of end product. Similarly the diazonium salt itself may be separated and reacted with the alcohol instead of the aqueous diazotization solution being reacted therewith (Saunders, "The Aromatic diazo compounds" (E. Arnold & Co., London 1949), page 271). All these methods are unsatisfactory on an industrial scale as regards economy and simplicity of operation with the highest possible yield of end product.

The synthesis of 3,5-dichlorobenzoic acid from 2-amino-3,5-dichlorobenzoic acid by reduction of the corresponding diazonium salt with hypophosphorous acid is described in J. Org. Chem., volume 17, page 367 (1952). The reaction is exothermic and proceeds violently and has to be carried out with a large excess of hypophosphorus acid at a very low temperature. This process is also not satisfactory as a reaction which is simple and reliable in operation or uses readily available substances, which is interesting on an industrial scale and which gives a high yield of end product.

The object of this invention is a new process for the production of dichlorobenzoic acids in a simpler and more economical way in better yields and higher purity.

We have now found that the production of a dichlorobenzoic acid of the formula (I):

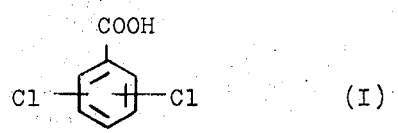

by reaction of an aromatic diazonium salt with an alcohol at elevated temperature is carried out more advantageously by reacting a diazonium salt of a dichloroaminobenzoic acid of the formula (II):

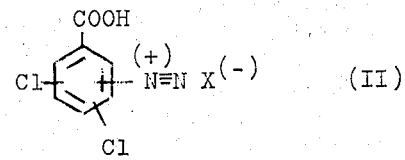

in which X is the anion of an acid, with a saturated aliphatic or araliphatic alcohol in an amount of from 1 to 10 moles per mole of starting material (II) in the presence of water in an amount of at least 100% by weight based on the alcohol.

When the diazonium chloride of 3,5-dichloroanthranilic acid and ethanol are used the reaction may be represented by the following equation:

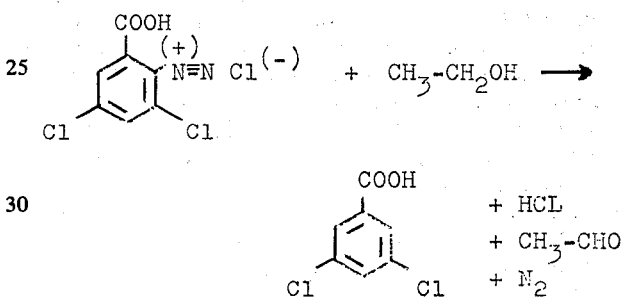

As compared with the prior art the process according to the invention gives dichlorobenzoic acids in better yields and purity, particularly on an industrial scale, in a simpler and more economical way. The formation of ethers or resinous byproducts is not observable to any significant extent. All these advantageous results are suprising in view of the teaching of the abovementioned publications that the exchange of the diazonium group should be carried out in the absence of water or in the least possible amount of water.

The diazonium compounds (II) are reacted with the alcohol in an amount of from 1 to 10 and preferably 1 to 3 moles of alcohol per mole of starting material (II). The alcohols may be monoalcohols or polyalcohols. Preferred alcohols are those of the formula (III):

$$ROH \quad (III)$$

in which R is alkyl of 1 to 5 carbon atoms or aralkyl of 7 to 12 carbon atoms or the radical $HO-R^1-$ in which $R^1$ is an aliphatic radical and particularly alkylene of 2 to 4 carbon atoms or the radical $R^2O-(R^1O)_n-R^1-$ in which the individual radicals $R^1$ may be identical or different and have the abovementioned general and preferred meanings of $R^1$ and $R^2$ is hydrogen or an aliphatic radical and particularly alkyl of one to four carbon atoms and n is one of the integers 4, 3 or 2 or particularly 1. The said radicals may also be substituted by groups which are inert under the reaction conditions, for example alkyl or alkoxy in each case of one to three carbon atoms.

Examples of alcohols (III) are methanol, ethanol, n-propanol, isopropanol, n-butanol- butanol-2, ethylene glycol, diethylene glycol, methylethylene glycol, benzyl alcohol, n-pentanol, phenylethanol, p-methylbenzyl alcohol, p-ethoxybenzyl alcohol, 1,3-propylene glycol, 1,4-butanediol, 1,2-propylene glycol, triethylene glycol, diethylene glycol mono-n-butyl ether or mixtures of the same.

The diazonium compounds may contain the diazonium group and/or the two chlorine atoms on any of the positions of the nucleus; the preferred starting material (II) is the diazonium salt of 2-amino-3,5-dichlorobenzoic acid and consequently the preferred end product (I) is 3,5-dichlorobenzoic acid. In the preferred starting materials (II) the X may be the anion of an organic or preferably an inorganic acid, for example a hydrogen sulfate, sulfate, nitrate or particularly a chloride. Examples of suitable diazonium compounds are:

1,3-dichloro-6-carboxybenzene-2-diazonium chloride, sulfate or hydrogen sulfate, the corresponding diazonium salts of 2-amino-4,6-dichlorobenzoic acid, 2-amino-3,6-dichlorobenzoic acid, 3-amino-2,6-dichlorobenzoic acid, 4-amino-3,5-dichlorobenzoic acid or 4-amino-2,6-dichlorobenzoic acid.

The reaction is carried out as a rule at a temperature of 40°C up to the boiling temperature of the mixture, conveniently from 50° to 200°C and preferably from 50° to 100°C at atmospheric or superatmospheric pressure, continuously or batchwise. The reaction is carried out in the presence of water in an amount of at least 100%, advantageously from 100 to 6000% and preferably from 2000 to 4000% by weight based on alcohol. It is possible although not necessary to allow the reaction mixture to react in the presence of metals, oxides or metal salts, for example copper powder, copper(I) oxide, copper(II) sulfate or a zinc salt such as zinc chloride or with simultaneous exposure to ultraviolet light.

The reaction may be carried out as follows:

The amine corresponding to the starting material (II) is diazotized by a conventional method, for example according to one of the methods described in Ullmanns Encyklopädie der technischen Chemie, volume 5, pages 791 et seq. It is preferred to diazotize the amine in aqueous mineral acid solution with an aqueous solution of sodium nitrite at a temperature of from 0° to 18°C for 15 to 70 minutes. The amount of water is conveniently determined by the production of the diazonium salt. Any nitrite remaining in the mixture is then destroyed by a conventional method, for example by adding urea. The diazotization solution thus obtained is then united at the said reaction temperature with the alcohol (III), if desired mixed with water and the abovementioned additive and it is convenient to allow the aqueous diazonium salt solution or diazonium salt suspension to flow into a preheated mixture of alcohol (III) and water or to allow the mixture of aqueous diazonium salt solution or diazonium salt suspension and alcohol to flow into preheated water. The reaction mixture is allowed to remain for 15 minutes to 2 hours at the reaction temperature while mixing well, the temperature being raised if desired towards the end of the reaction, after which the end product is isolated by a conventional method, for example by filtration.

The compounds which can be prepared according to the process of the invention are valuable starting materials for the production of pharmaceutical preparations, dyes and pest control agents. The abovementioned publications, British patent specification No. 819,127, U.S. Pat. No. 3,553,274 and Ullmanns Encyklopädie der technischen Chemie, volume 4, page 287, may be referred to concerning the use of the said compounds.

The following Examples illustrate the invention. The parts specified in the Examples are by weight.

EXAMPLE 1

206 parts of 2-amino-3,5-dichlorobenzoic acid is introduced into 1000 parts of water, then 180 parts of 50% by weight caustic soda solution and 70 parts of sodium nitrite are added and the mixture is allowed to flow while cooling into a mixture of 200 parts of water and 600 parts of concentrated hydrochloric acid (25% by weight strength). The mixture is stirred for another hour, 20 parts of urea is added and the whole is allowed to flow at 65°C with vigorous evolution of nitrogen into a mixture of 70 parts of methanol, 400 parts of water and 3 parts of copper(II) sulfate. The mixture is stirred for another 25 minutes, cooled to ambient temperature and suction filtered. 183 parts (96% of theory) of 3,5-dichlorobenzoic acid is obtained having a melting point of 179° to 181°C.

EXAMPLE 2

A solution of the diazonium prepared as described in Example 1 from 206 parts of 3,5-dichloroanthranilic acid is allowed to flow into a mixture of 90 parts of isopropanol, 400 parts of water and 3 parts of copper powder at 70°C. The mixture is stirred for another hour, cooled, suction filtered and the filter cake is dried. The yield is 186 parts (97% of theory) of 3,5-dichlorobenzoic acid. Melting point: 178° to 180°C.

EXAMPLE 3

The reaction described in Example 2 is carried out with 90 parts of n-propanol. 172 parts (90% of theory) of 3,5-dichlorobenzoic acid is obtained having a melting point of 176° to 178°C.

EXAMPLE 4

144 parts of 50% by weight caustic soda solution and 80 parts of ethanol are added to a mixture of 165 parts of 3,5-dichloroanthranilic acid and 1400 parts of water. 56 parts of sodium nitrite is added to the clear solution and the mixture is cooled to 10° to 15°C. Diazotization is carried out by slowly adding 400 parts of concentrated hydrochloric acid. The mixture is stirred for another hour, 16 parts of urea and 2 parts of copper(II) sulfate are added and the mixture is allowed to flow within 15 minutes into 200 parts of water at 70°C. Thirty minutes later the whole is cooled to ambient temperature and the end product is isolated by suction filtration. The yield is 148 parts (97% of theory) of 3,5-dichlorobenzoic acid having a melting point of 178° to 180°C.

EXAMPLE 5

200 parts of ethanol is slowly added to a solution, heated to 70°C, of the diazonium salt prepared as described in Example 1 from 412 parts of 3,5-dichloroanthranilic acid; elimination of nitrogen immediately takes place with evolution of heat. The mixture is stirred for another 15 minutes and 350 parts (92% of theory) of 3,5-dichlorobenzoic acid having a melting point of 176° to 178°C is isolated as described in Example 1.

EXAMPLE 6

The reaction as described in Example 1 is carried out with 60 parts of glycol in 350 parts of water. 174 parts (91% of theory) of 3,5-dichlorobenzoic acid is obtained having a melting point of 179° to 181°C.

EXAMPLE 7

The reaction mixture prepared as described in Example 1 from 206 parts of 3,5-dichloroanthranilic acid is allowed to flow into a mixture of 100 parts of methyl glycol, 400 parts of water and 2 parts of copper(II) sulfate at 60° to 70°C. As described in Example 1, 170 parts (89% of theory) of 3,5-dichlorobenzoic acid having a melting point of 178° to 179°C is obtained.

We claim:

1. A process for the production of a dichlorobenzoic acid of the formula

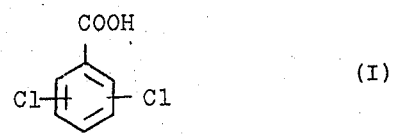

which comprises:
reacting at an elevated temperature the diazonium salt of a dichloroaminobenzoic acid of the formula

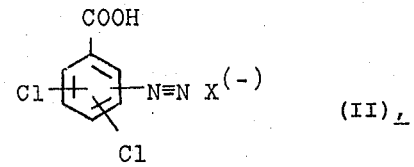

in which X is the anion of an acid, with a saturated aliphatic or araliphatic alcohol in an amount of from 1 mole to 10 moles per mole of starting material (II) in the presence of water in an amount of at least 100% by weight based on the alcohol.

2. A process as claimed in claim 1 wherein the reaction is carried out with from 1 mole to 3 moles of alcohol per mole of starting material (II).

3. A process as claimed in claim 1 wherein the reaction is carried out with a hydrogen sulfate, sulfate, nitrate or chloride of the diazonium compound of 2-amino-3,5-dichlorobenzoic acid, 2-amino-4,6-dichlorobenzoic acid, 2-amino-3,6-dichlorobenzoic acid, 3-amino-2,6-dichlorobenzoic acid, 4-amino-3,5-dichlorobenzoic acid, 4-amino-2,6-dichlorobenzoic acid, or 3-amino-2,4-dichlorobenzoic acid.

4. A process as claimed in claim 1 wherein the reaction is carried out at a temperature of from 40°C to the boiling temperature of the mixture.

5. A process as claimed in claim 1 carried out at a temperature of from 50° to 200°C.

6. A process as claimed in claim 1 carried out at a temperature of from 50° to 100°C.

7. A process as claimed in claim 1 wherein the reaction is carried out in the presence of water in an amount of from 100 to 6000% by weight based on alcohol.

8. A process as claimed in claimed 1 wherein the reaction is carried out in the presence of from 2000 to 4000% by weight of water based on alcohol.

9. A process as claimed in claim 1 wherein the alcohol has the formula ROH in which:
R is alkyl of 1 to 5 carbon atoms or aralkyl of 7 to 12 carbon atoms or one of the radicals $HO-R^1-$ or $R^2O-(R^1O)_n-R^1-$ wherein each $R^1$ is alkylene of 2 to 4 carbon atoms,
$R^2$ is hydrogen or alkyl of one to four carbon atoms and
$n$ is 1, 2, 3 or 4.

10. A process as claimed in claim 9 wherein the reaction is carried out at a temperature of from 40°C. to the boiling temperature of the mixture.

11. A process as claimed in claim 9 wherein the reaction is carried out in the presence of water in an amount of from 100 to 6000% by weight based on the alcohol.

* * * * *